(12) United States Patent
Nguyen et al.

(10) Patent No.: US 11,747,456 B2
(45) Date of Patent: Sep. 5, 2023

(54) LOCATION DEVICE AND SYSTEM FOR LOCATING AN ULTRASOUND ACOUSTIC SENSOR

(71) Applicant: KONINKLIJKE PHILIPS N.V., Eindhoven (NL)

(72) Inventors: Man Nguyen, Melrose, MA (US); Hua Xie, Cambridge, MA (US); Sheng-Wen Huang, Ossining, NY (US); Carolina Amador Carrascal, Everett, MA (US); Vijay Thakur Shamdasani, Kenmore, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 890 days.

(21) Appl. No.: 16/492,446

(22) PCT Filed: Mar. 1, 2018

(86) PCT No.: PCT/EP2018/054999
§ 371 (c)(1),
(2) Date: Sep. 9, 2019

(87) PCT Pub. No.: WO2018/162305
PCT Pub. Date: Sep. 13, 2018

(65) Prior Publication Data
US 2020/0041630 A1    Feb. 6, 2020

Related U.S. Application Data

(60) Provisional application No. 62/577,198, filed on Oct. 26, 2017, provisional application No. 62/469,592, filed on Mar. 10, 2017.

(30) Foreign Application Priority Data

Mar. 10, 2017   (EP) ..................... 17160264

(51) Int. Cl.
*A61B 34/20* (2016.01)
*G01S 7/52* (2006.01)
(Continued)

(52) U.S. Cl.
CPC .......... *G01S 7/52085* (2013.01); *A61B 34/20* (2016.02); *G01S 7/52036* (2013.01);
(Continued)

(58) Field of Classification Search
CPC . G01S 7/52085; G01S 7/52036; A61B 34/20; A61B 2034/2063
See application file for complete search history.

(56) References Cited

U.S. PATENT DOCUMENTS 4,161,122 A * 7/1979 Buchner .............. G10K 11/346
                                                          73/626
4,249,539 A    2/1981 Vilkomerson et al.
(Continued)

FOREIGN PATENT DOCUMENTS

| CN | 102879472 A | 1/2013 |
|----|-------------|--------|
| WO | 2004107963 A2 | 12/2004 |
| WO | 2010033875 A1 | 3/2010 |

OTHER PUBLICATIONS

International Search Report and Written Opinion for International Application No. PCT/EP2018/054999, filed Mar. 1, 2018, 14 pages.

*Primary Examiner* — Serkan Akar
*Assistant Examiner* — Amal Aly Farag (57) ABSTRACT

A location device is provided for determining the location of an acoustic sensor. A location process makes use of a plurality of transmit beams (wherein a beam is defined as a transmission from all transducers of an ultrasound array), with a frequency analysis to identify if there is a signal reflected from the acoustic sensor. A location is obtained from the plurality of frequency analyses.

17 Claims, 3 Drawing Sheets

(51) Int. Cl.
*A61B 90/00* (2016.01)
*A61B 8/00* (2006.01)

(52) U.S. Cl.
CPC ..... *A61B 8/4263* (2013.01); *A61B 2034/2063* (2016.02); *A61B 2090/3784* (2016.02)

(56) References Cited

U.S. PATENT DOCUMENTS

| | | | |
|---|---|---|---|
| 4,697,595 | A | 10/1987 | Breyer et al. |
| 5,092,336 | A | 3/1992 | Fink |
| 6,587,709 | B2 | 7/2003 | Solf et al. |
| 6,685,645 | B1 | 2/2004 | McLaughlin et al. |
| 8,622,909 | B1 * | 1/2014 | O'Ruanaidh .......... A61B 8/085 600/407 |
| 9,282,946 | B2 | 3/2016 | Vignon et al. |
| 2004/0193042 | A1 * | 9/2004 | Scampini ............ G01S 7/52095 600/437 |
| 2004/0211260 | A1 | 10/2004 | Girmonsky et al. |
| 2006/0085049 | A1 | 4/2006 | Cory et al. |
| 2008/0255452 | A1 | 10/2008 | Entrekin |
| 2012/0179046 | A1 | 7/2012 | Kabakov et al. |
| 2013/0217997 | A1 | 8/2013 | Byrd et al. |
| 2013/0296701 | A1 | 11/2013 | Zalev et al. |
| 2014/0094695 | A1 | 4/2014 | Jain et al. |
| 2015/0223778 | A1 * | 8/2015 | Honjo ...................... A61B 8/54 600/447 |
| 2015/0359512 | A1 * | 12/2015 | Boctor ................ G01S 15/8997 600/447 |
| 2016/0128668 | A1 | 5/2016 | Jain et al. |

* cited by examiner

LOCATION DEVICE AND SYSTEM FOR LOCATING AN ULTRASOUND ACOUSTIC SENSOR

RELATED APPLICATIONS

This application is the U.S. National Phase application under 35 U.S.C. § 371 of International Application No. PCT/EP2018/054999, filed on Mar. 1, 2018, which claims the benefit of European Application No. 17160264.2, filed Mar. 10, 2017, and of both Provisional Application Ser. No. 62/469,592, filed Mar. 10, 2018, and Provisional Application Ser. No. 62/577,198, filed Oct. 26, 2017. These applications are hereby incorporated by reference herein.

FIELD OF THE INVENTION

This invention relates to a device and method for locating an acoustic sensor, for example for locating an implanted object within a subject. This is of interest for guidewire, catheter or needle tip tracking, and hence guided vascular access generally.

BACKGROUND OF THE INVENTION

Needles, catheters and other interventional tools are often difficult to visualize under ultrasound due to their specular nature and unfavorable incidence angles. One solution for marking a needle tip under ultrasound guidance is to embed a small acoustic (ultrasound) sensor at the tip of the needle. Such a sensor receives the direct ultrasound signals that impinge upon it as imaging beams from an ultrasound imaging probe sweep the field of view. A sensor may also be implanted in the body, for monitoring a condition in the body.

An acoustic sensor device in general has a membrane which deforms in response to an external stimulus, and has a resonance frequency. It can receive and emit acoustic signals with a certain frequency spectra. The resonance frequencies of the sensor device are dependent on the characteristics of the device, for example the internal pressure of the membrane acoustic sensor, or size and material of the device. The external environment also affects the device resonance frequencies. As a result, information about the external environment can be extracted from the resonance frequencies generated by the sensor.

The acoustic sensor device may function solely for location, by generating an identifiable signal at its location. However, by calibrating the frequency response of the sensor, information about the external environment (such as the pressure in a fluid flow field) can also be encoded in the signal received from the acoustic sensor. For example, for pressure sensors, the relationship between the device resonance frequency and the ambient pressure can be calibrated. Based on the frequency detected, the ambient pressure around the device can be determined.

Different ways of using the signals received from the sensor to highlight the position of the sensor in the ultrasound image have been proposed. These rely on time-of-flight of ultrasound from the imaging probe to the sensor for estimating the range coordinate of the sensor, and on the intensity of the received signals as the imaging beams sweep the field of view to recover the lateral coordinate.

The acoustic sensor device is often implanted with other interventional devices such as stents or prosthetic heart valves. As a result, it is challenging to locate the device under B-mode ultrasound.

Ultrasound array transducers may be configured as a one-dimensional (ID) array for imaging a two dimensional (2D) image plane, or as a two dimensional (2D) array of transducer elements for imaging a three dimensional region. A 2D array comprises elements extending in both azimuth and elevation directions which can be operated fully independently to both focus and steer beams in any azimuth or elevation direction. These arrays can be configured in either flat or curved orientations.

Each element of the transducer array is individually controlled on transmit and receive using transmit and receive beamforming. A 2D array may have 100-200 rows of elements in one dimension and 100-200 columns of elements in the other dimension, totaling thousands of individual elements. To cope with the number of elements, a microbeamformer integrated circuit can be attached to the transducer array which performs partial beamforming of groups of elements referred to as patches. The individually delayed and summed signals of each patch are conducted over a standard size cable to the ultrasound system beamformer where the summed signal from each patch is applied to a channel of the system beamformer, which completes the beamforming operation.

It is known to make use of a 2D ultrasound transducer array to provide imaging of a volumetric region of interest by electronically modifying the beamforming (instead of mechanically moving the probe) which has advantages of high frame rates, efficient workflow, and robust elevation focusing. Parallel beamforming approaches allow fast imaging. The electronic control of the beamforming also enables plane wave beams, diverging wave beams as well as focusing beams to be transmitted.

There remains a need for an approach which enables effective location of an acoustic sensor using an ultrasound transducer, for example before extracting information regarding the surrounding environment. It would therefore be desirable to make use of the capabilities of electronic beamforming control to provide an improved location approach.

SUMMARY OF THE INVENTION

The invention is defined by the claims.

According to examples in accordance with an aspect of the invention, there is provided a location device for determining the location of an acoustic sensor, comprising:

an ultrasound transducer array arranged to transmit a plurality of ultrasound beams and receive corresponding reflected echo signals;
a controller arrangement, comprising:
  a transmit controller for controlling the transmitted signals of the transducer array to provide a transmit beam comprising a transmission from each transducer of the array;
  a receive controller for analyzing the received reflected signals,
wherein the controller arrangement is adapted to implement a location process which comprises, for each of the plurality of transmitted ultrasound beams, performing a frequency analysis to identify if there is a signal reflected from the acoustic sensor and to identify a location area, and to derive a progressively more accurate final location within said location area from the plurality of frequency analyses.

By performing a set of analyses, for each of a plurality of transmit beams, more accurate location information may be obtained. The device makes use of an adaptive transmit beam pattern to precisely locate an acoustic sensor.

In this way, the device is able to reduce the uncertainty and improve the workflow in locating the acoustic sensor. The transmit beams can be steered and swept electronically without the transducer being mechanically moved.

The final location is obtained in a manner which progressively increases accuracy. By this is meant that location information is first obtained with a relatively low precision (i.e. identifying only a location area), and then a different imaging approach is conducted using that coarse location area information to obtain a higher precision location. The scanning approaches may be of different types (such as unfocused and focused) or they may be of the same type but with different scanning parameters (such as different density of scan lines). Overall, the aim is to enable a high precision location to be identified in a way which reduces the amount of time and/or image processing required to reach the desired location accuracy.

In one set of examples, the controller arrangement is adapted to implement a location process which comprises:

providing a first, non-focused, transmit beam and obtaining a first location area;

providing at least one further, focused, transmit beam for a smaller region of interest within the first location area and obtaining at least one more accurate location.

In this process, the accuracy of the location is increased in iterative steps, making use of an adaptive transmit pattern. The pattern starts as a non-focused beam such as a broad beam pattern and narrows to a focused beam based on the receive beams that have components of the resonant signals from the acoustic sensor. The broad beam pattern provides a coarse location (i.e. a location area) and the spatial resolution and bandwidth of the focused beam allows a more precise location to be determined.

The controller arrangement may be adapted to implement a location process which comprises iteratively providing multiple transmit beams for successively smaller regions of interest with successively smaller depths of field and obtaining successively more accurate locations. As the depth of field is reduced, the sensor location is closer and closer to the focal point of the transmit beam.

In a second set of examples, the controller arrangement is adapted to implement a location process which comprises scanning a first plurality of focused transmit beams across a region of interest to provide focusing positions with a first spacing (first beam density), and scanning at least a second plurality of focused transmit beams across the region of interest to provide more closely spaced focusing positions (more densely packed scanning lines). The higher first spacing corresponds to a lower precision of the first location area, whereas the more closely spaced focusing positions correspond to a more precise location. Acquiring each scanning line takes time, therefore, this embodiment permits faster defining the first location with a course precision; and further scanning a smaller region of interest within the first location area with more densely packed scanning beams (lines), thereby obtaining with further accuracy a further location of the acoustic sensor without investing additional time.

In this way, beams that carry signals specific to the acoustic sensor are identified from a lower resolution sweep, and from this information, a more accurate location may be found from a higher resolution sweep.

The controller arrangement may be further adapted to identify an orientation of the acoustic sensor. This can be achieved for a membrane of the acoustic sensor, since the membrane resonance results in a normally directed echo signal. Based on knowledge of the transmit beam direction and the associated received echo signal both the location of the acoustic sensor and its membrane orientation may be derived.

The controller arrangement is thus for example adapted to identify an orientation of the acoustic sensor by determining a transmission angle and emission (reflection) angle for which the received echo (or signal corresponding to said reflection angle) is strongest.

The device may comprise an output for directing the user to move the ultrasound transducer array to a location which gives the strongest location signal characteristic to the acoustic sensor reflection. This may be directly above the acoustic sensor, but for an angled acoustic sensor the transducer array location may be offset from the acoustic sensor so that the transmit beam is directed normally to the membrane and the receive beam is received from the same normal direction.

In this way, the sensitivity of the location process is improved, based on transmit and receive beamforming to maximize the acoustic pressure reaching the acoustic sensor as well as maximizing the beamsum data provide by the receive beamforming process.

The transducer array preferably comprises a 2D array of transducer elements, for 3D localization.

The invention also provides a location system comprising:

an acoustic sensor; and a location device as defined above.

The acoustic sensor for example comprises a membrane having a resonant frequency within a reception frequency range of the acoustic transducer array, for generating an echo at the resonant frequency.

The invention also provides a method of locating an acoustic sensor, comprising:

controlling the transmission of ultrasound signals of a transducer array to provide a transmit beam comprising a transmission from each transducer of the array; and analyzing received reflected signals, wherein the method comprises, for each of a plurality of transmit beams, performing a frequency analysis to identify if there is a signal reflected from the acoustic sensor and to determine a location area, and to derive a progressively more accurate final location within the location area from the plurality of frequency analyses.

This approach enables an accurate location to be obtained in a short time, based on combining multiple imaging processes.

In one set of examples, the method comprises:

providing a first, unfocused, transmit beam and obtaining a first location area;

providing at least one further, focused, transmit beam for a smaller region of interest within the first location area and obtaining at least one more accurate location.

In another set of examples, the method comprises:

scanning a first plurality of focused transmit beams across a region of interest to provide focusing positions with a first spacing; and scanning at least a second plurality of focused transmit beams across the region of interest to provide more closely spaced focusing positions.

An orientation of the acoustic sensor may also be obtained by determining a transmission angle and corresponding reflection angle for which the received echo is strongest, and directing the user to move the ultrasound transducer array to a location which gives the strongest location signal.

The invention may be implemented at least in part in computer software.

These and other aspects of the invention will be apparent from and elucidated with reference to the embodiment(s) described hereinafter.

BRIEF DESCRIPTION OF THE DRAWINGS

Examples of the invention will now be described in detail with reference to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a location device for determining the location of an acoustic sensor. A location process makes use of a plurality of transmit beams (wherein a beam is defined as a transmission from all transducers of an ultrasound array), with a frequency analysis to identify if there is a signal reflected from the acoustic sensor. A location is obtained from the plurality of frequency analyses, by obtaining a location with progressively increasing resolution and hence accuracy.

The invention makes use of adaptive beamforming.

Transmit beamforming involves providing delays in the transmitted ultrasound signals from a transducer array in order to create an interference pattern in which the majority of the signal energy propagates in one angular direction. Adaptive transmit beamforming enables different interference patterns to be created, including plane wave propagation, or a focused beam directed to a specific point, and at a particular depth from the ultrasound transducer array.

Receive beamforming involves adjusting the amplitude and delays of the received signal on each element in order to measure reception from a chosen angular direction. Thus, to build up an image, receive beamforming is applied for the transducer array in respect of each point in turn to derive the signal intensity received from that point.

An image is formed by combining multiple transmit scan lines, where one scan line is a transmitted and received narrow beam. By combining the received echo data for the set of limes the ultrasound image is created.

For the purposes of this document, a "transmit beam" is meant to indicate the acoustic pressure field that is emitted from a set of transducer elements. The transmit beam can use all transducer elements or a sub-set of elements, depending on the design (imaging depth, resolution, etc.). The shape of the transmit beam can also vary, for example it may have a focus or no focus (e.g. a divergent beam or a plane wave beam).

The general architecture of an ultrasound imaging system will first be described, with reference to FIG. 1 which shows an ultrasonic diagnostic imaging system 2 with an array transducer probe 4 in block diagram form.

The array transducer probe 4 comprises an ultrasound transducer array 6 of transducer cells 8. Traditionally, piezoelectric materials have been used for ultrasonic transducers. Examples are lead zirconate titanate (PZT) and polyvinylidene difluoride (PVDF) materials, with PZT being particularly popular as the material of choice. Single crystal piezoelectric materials are used to achieve high piezoelectric and electro-mechanical coupling constants for high performance transducers.

Recent developments have led to the prospect that medical ultrasound transducers can be batch manufactured by semiconductor processes. Desirably these processes should be the same ones used to produce the application specific integrated circuits (ASICs) needed by an ultrasound probe such as a CMOS process, particularly for 3D ultrasound. These developments have produced micro machined ultrasonic transducers or MUTs, the preferred form being the capacitive MUT (CMUT). CMUT transducers are tiny diaphragm-like devices with electrodes that convert the sound vibration of a received ultrasound signal into a modulated capacitance.

CMUT transducers in particular are able to function over a broad bandwidth, enable high resolution and high sensitivity imaging, and produce a large pressure output so that a large depth of field of acoustic signals can be received at ultrasonic frequencies.

Figure 1:
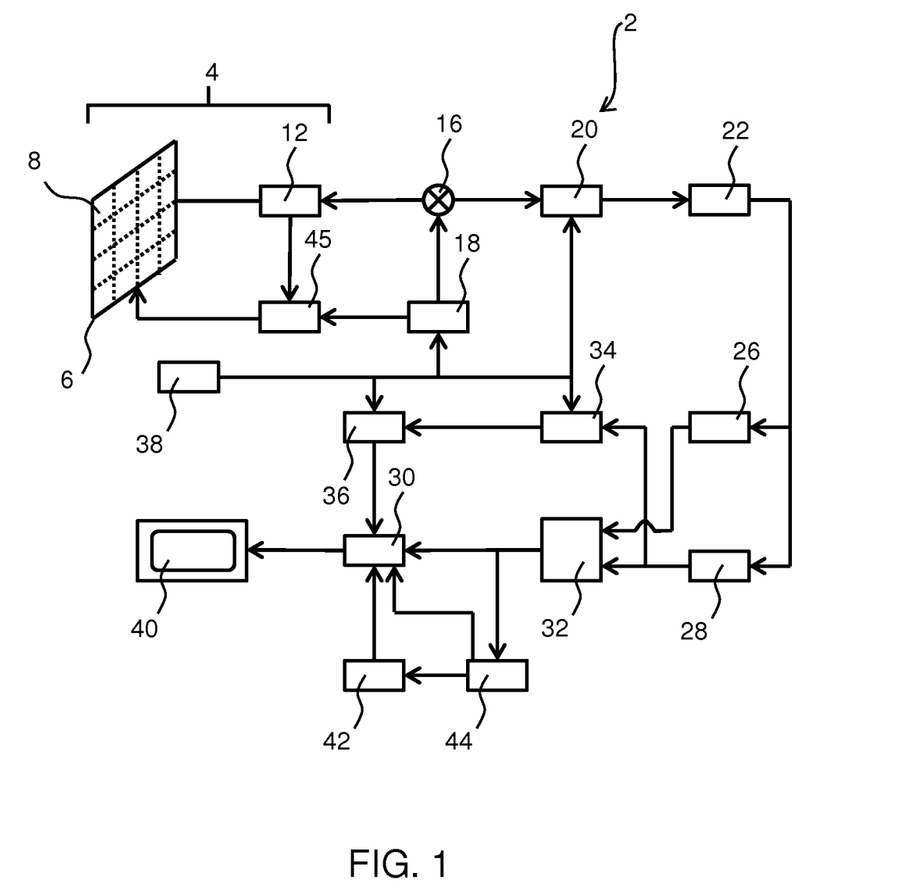
FIG. 1 shows a known ultrasound imaging system.

FIG. 1 shows the transducer array 6 of the transducer (CMUT) cells 8 as discussed above for transmitting ultrasonic waves and receiving echo information. The transducer array 6 of the system 2 may generally be a one- or a two-dimensional array of transducer elements capable of scanning in a 2D plane or in three dimensions for 3D imaging.

The transducer array 6 is coupled to a micro-beamformer 12 which controls transmission and reception of signals by the transducer cells 8. Micro-beamformers are capable of at least partial beam forming of the signals received by groups or "patches" of transducer elements for instance as described in U.S. Pat. No. 5,997,479 (Savord et al.), U.S. Pat. No. 6,013,032 (Savord), and U.S. Pat. No. 6,623,432 (Powers et al.)

The micro-beamformer 12 is coupled by the probe cable, e.g. coaxial wire, to a transmit/receive (T/R) switch 16 which switches between transmission and reception modes and protects the main beam former 20 from high energy transmit signals when a micro-beamformer is not present or used and the transducer array 6 is operated directly by the main beam former 20. The transmission of ultrasonic beams from the transducer array 6 under control of the micro-beamformer 12 is directed by a transducer controller 18 coupled to the micro-beamformer by the T/R switch 16 and the main beam former 20, which receives input from the user's operation of the user interface or control panel 38. One of the functions controlled by the transducer controller 18 is the direction in which beams are steered and focused. Beams may be steered straight ahead from (orthogonal to) the transducer array 6, or at different angles for a wider field of view.

The transducer controller 18 may be coupled to control a voltage source 45 for the transducer array 6. For instance, the voltage source 45 sets DC and AC bias voltage(s) that are applied to CMUT cells 8 of the transducer array 6, e.g. to generate the ultrasonic RF pulses in transmission mode.

The partially beam-formed signals produced by the micro-beamformer 12 are forwarded to the main beam former 20 where partially beam-formed signals from individual patches of transducer elements are combined into a fully beam-formed signal. For example, the main beam former 20 may have 128 channels, each of which receives a partially beam-formed signal from a patch of dozens or hundreds of the transducer cells 8. In this way the signals received by thousands of transducer elements of a transducer array 6 can contribute efficiently to a single beam-formed signal.

The beam-formed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination. The bandpass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B-mode processor 26 and optionally to a Doppler processor 28. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) are coupled to a scan converter 32 and a multiplanar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user interface or control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface or control panel 38, such as patient name.

The user interface is also coupled to the transducer controller 18 to control the generation of ultrasound signals from the transducer array 6 and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the micro-beamformer 12 may be omitted, the ultrasound probe 4 may not have 3D imaging capabilities and so on. Other variations will be apparent to the skilled person.

Figure 2A:
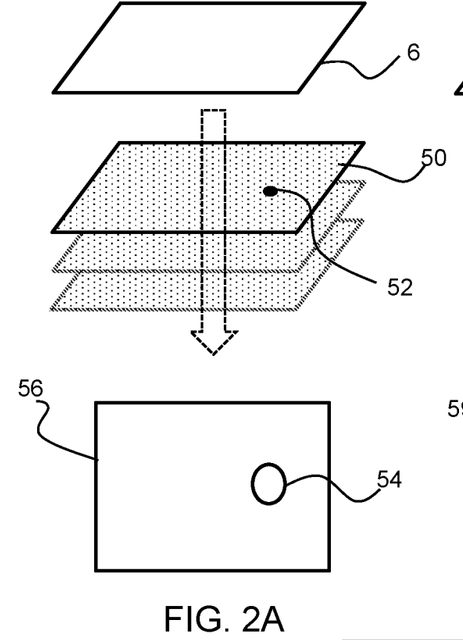
FIGS. 2A, 2B and 2C show a first example of a location process using the system of FIG. 1.
Figure 2B:
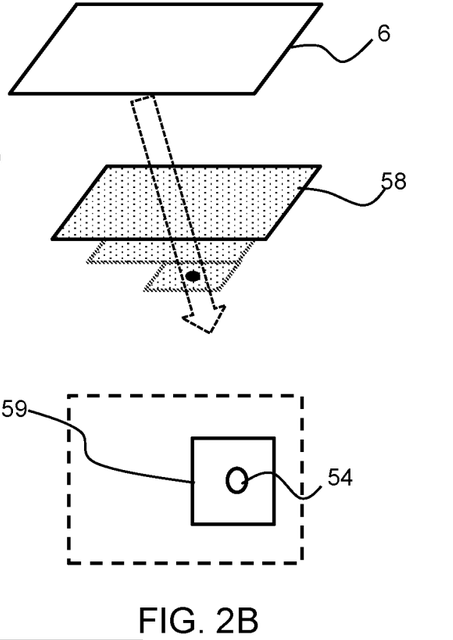
Figure 2C:
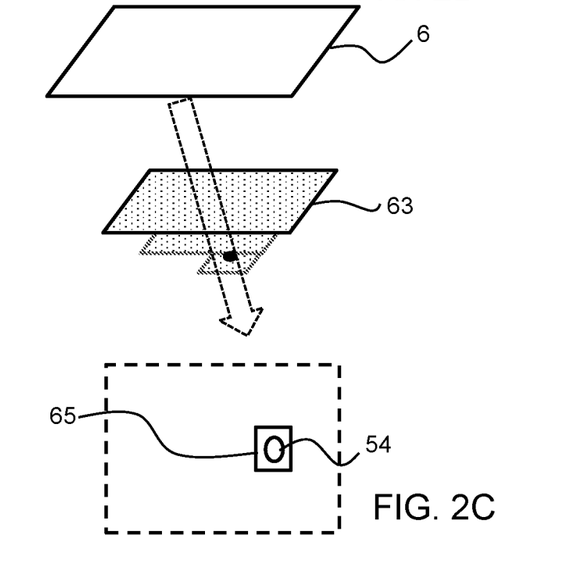

FIGS. 2A, 2B and 2C are used to show a first example of a location process.

FIG. 2A shows the transducer array 6 generating a plane wave transmit beam 50. The implanted acoustic sensor is shown as 52.

The acoustic sensor 52 comprises a membrane, having a resonant frequency within the band pass frequency band of the receiver of the system 2, for example within 1 to 5 MHz.

The emitted ultrasound excites the membrane of the acoustic sensor 52, which then generates an echo signal at its resonant frequency. The resonance frequency of the acoustic sensor 52 will depend on the surrounding environment, such as the pressure. The acoustic signals emitted from the acoustic sensors 52 will have frequency components of the incident signals transmitted from the transducer array 6 and of the resonant frequency of the acoustic sensor 52, and shifted frequency components compared to the signals transmitted from the ultrasound transducer array 6. While the components of the resonant frequency of the acoustic sensor 52 do not necessarily need to be in the frequency bandwidth covered by the ultrasound transducer array 6, the shifted frequency components will be. By detecting the presence of shifted frequency components in each receive beam, the location of the acoustic sensor 52 can be identified. The frequency components of the received signals are typically analyzed using the Fourier Transform. Furthermore, by calculating how much the emitted frequency from the acoustic sensor is shifted, the resonant frequency can be determined. As previously mentioned, this resonant frequency carries information about the surrounding pressure.

The acoustic sensor 52 responds to an incident acoustic wave by generating a resonant echo signal. By way of example, the acoustic sensor 52 may be of the type disclosed in US 2013/0060139. The acoustic sensor 52 may be used for pressure monitoring, based on changes in the frequency response of the acoustic sensor 52 to local pressure variations.

This invention is concerned in particular with locating the acoustic sensor 52. The obtaining and processing of a sensor reading may be performed in known manner and as described above.

Among the received beams, there is a set for which the resonant frequency of the acoustic sensor 52 is detected based on frequency analysis (i.e. Fourier Transform analysis). Those receive beams are indicated by region 54 within an image 56 representing the spatially received beams. The image 56 represents elevation versus azimuth.

Thus, the received beams of FIG. 2A are obtained based on providing a first, plane wave, transmit beam, and from this the region 54 defines a first obtained location for the acoustic sensor 52. This first obtained location is a general location area, of lower precision than is required. For the plane wave beam, delays may be applied to steer the plane-waves to different angles or to adjust how much the beams are diverging.

For the unfocused (e.g. plane wave) beam imaging, the emitted acoustic signals (beams) cover larger areas. For each of these transmit beams, a large field of view can be generated (with lower quality compared to focused-beam imaging). However, by coherently summing these large individually reconstructed fields of view (FOVs), a final image can be generated with image quality comparable to a transmit-focused beam. The advantages of unfocused beam imaging include faster frame rate (less transmits required to reconstruct the whole image) but at the cost of increased system complexity because more parallel-line processing is required to reconstruct the larger field of view.

The transmit and receive elements used for one transmit beam can include multiple rows and columns of the 2D transducer array. The signals received are stored and then used for beamforming.

The received echo signals from the acoustic sensor will be received at multiple elements of the transducer array. These signals arrive at the elements at different times, based on the travelling paths. Therefore, during subsequent receive beamforming, the location of the source signals can be identified. The receive beamforming takes place for every point in the field of view and comprises a delay-and-sum operation for the employed set of transducer elements. The received signals may have different amplitudes and frequencies, from which the location of the acoustic sensor can be identified but also information about the environment outside the sensor (i.e. making use of the pressure sensing functionality of the implanted acoustic sensor).

After the plane wave transmit beam 50 has been processed, a focused transmit beam 58 is formed as shown in FIG. 2B. This focuses to a point behind the coarse sensor location as determined by the plane wave imaging. The focusing is achieved by transmit beamforming.

The focused-beam imaging is for example based on a scan line approach whereby the imaging is performed as a sequence of scan lines, each of which has a single focus. The received echo information is used to build up an image progressively as a set of scan lines.

This approach provides the first focused transmit beam 58 for a smaller region of interest. From this, a more accurate location within the location area found in FIG. 2A is found, as shown as pane 59.

This process may be repeated iteratively so that a second focused transmit beam 63 is provided as shown in FIG. 2C resulting in a more focused beam around the region 54. This yields improved location as shown in pane 65, wherein the region 54 again represents the location of the receive beams that contain the resonant signals from the sensor.

Thus, in this way, the transmit beam starts as a broad beam in-plane pattern and progressively narrows down to a focused beam based on the receive beams that have the components of resonance signals from the acoustic sensor. This adaptive transmit pattern provides a quick way to locate the acoustic sensor. While the broad beam provides a coarse location of the acoustic sensor at the beginning of the location process, the greater spatial resolution and smaller beam width of the focusing beams allow more precise location.

The approach of FIGS. 2A-2C may also be used to detect movement of the acoustic sensor, by comparing the received sensor signal location from one transmit beam with the received sensor signal location from previous transmit beams. If there is no overlap between them, it indicates that the acoustic sensor has moved to a different location. The regions 54 show the possible locations of the acoustic sensor in the different images. As the transmit beam pattern changes (un-focused beams become closer and closer to focused beams), the regions 54 should become smaller giving a more precise location, and hence they should overlap (or be contained within) previous location regions. If there is no such overlap as the imaging process proceeds, it means the relative position between the external transducer and the internal acoustic sensor has changed, so the sequence should then be restarted with an un-focused transmit beam.

An alternative example is to sweep a transmit focus beam throughout the region of interest and identify the beams that carry signals specific to the acoustic sensor. A first sweep is at a lower resolution, for example with a transmit beam for every Nth scan line (e.g. every fifth scan line). From the scan lines for which an echo is received from the acoustic sensor, a higher resolution image may be obtained, for example based on a sub-set of adjacent scan lines (e.g. scan line numbers 10 to 15). There may then be a progressive increase in resolution if multiple scans are carried out. There may be exactly two imaging processes, but three imaging processes at progressively higher precision are also possible. In this context, an imaging process is to be understood as a number of transmit sequences to localize the acoustic sensor. For example, a first sequence may involve transmitting every 5 scan lines for the whole 3D volume. A second sequence may then involve transmitting every 3 scan lines with a smaller pane 59, and a third sequence then involves transmitting every scan lines for the final sequence with the smallest region 54.

The acoustic sensor will emit pressure waves which are stronger in a direction normal to the sensor membrane, and they will be set into resonance more strongly by an incident ultrasound wave which is directed normally to the membrane orientation. Thus, to receive a strongest location signal, the position of the ultrasound transducer may be selected taking into account an orientation and/or position of the acoustic sensor.

For an acoustic sensor which remains relatively stationary, it may be desirable to reposition the ultrasound transducer array to obtain the best signal.

Figure 3A:
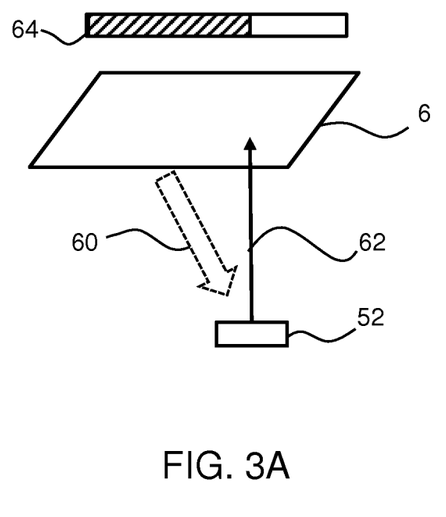
FIGS. 3A and 3B show a second example of a location process using the system of FIG. 1.
Figure 3B:
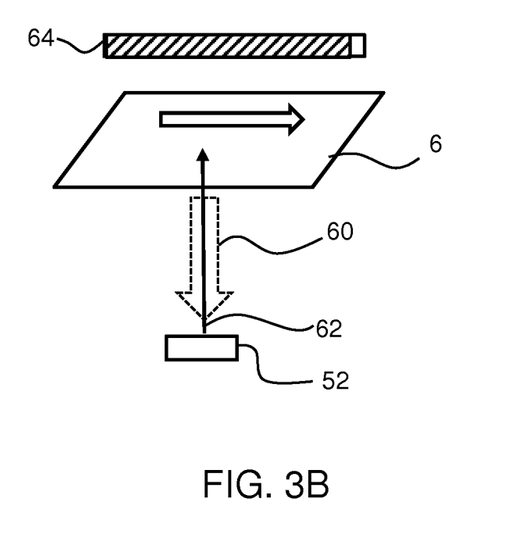

FIGS. 3A and 3B show a beam directed to an acoustic sensor 52 which is off-center to the ultrasound transducer array 6. FIG. 3A shows that the focused beam 60 is directed laterally so that it does not provide optimal excitation of the acoustic sensor 52 (assuming the acoustic sensor membrane plane is parallel to the plane of the transducer array). The reflected echo signal from the sensor echo is shown as 62.

The known directional angle of the focused beam 60 is used to derive an improved position of the transducer array. The user may then be instructed to move the ultrasound transducer array 6 to a better position shown in FIG. 3B.

An indicator 64 for example provides a measure of the resonant signal strength so that the user can be directed to move the transducer array 6 to obtain the best location signal.

The acoustic sensor 52 may not have its membrane parallel to the transducer array plane.

Figure 4A:
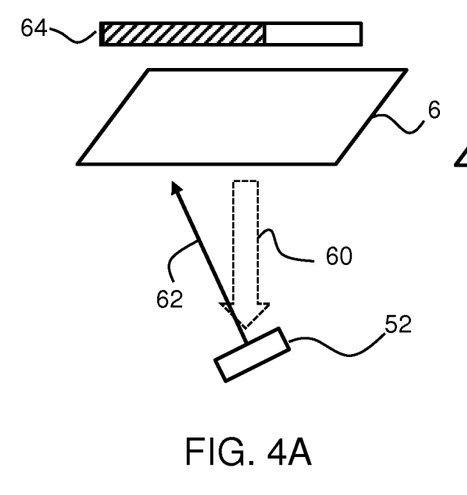
FIGS. 4A and 4B show a third example of a location process using the system of FIG. 1.
Figure 4B:
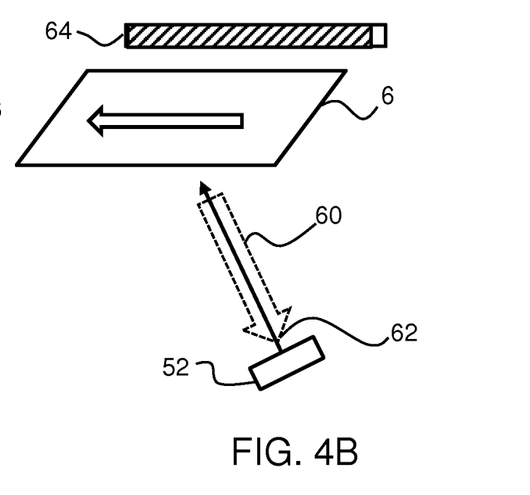

FIGS. 4A and 4B show a transmit beam directed to an acoustic sensor 52 which is central to the ultrasound transducer array 6 but the membrane is not parallel. FIG. 4A shows that the reflected echo signal 62 is directed laterally. The excitation of the resonance is not optimized.

The known directional angle of the received beam is used to derive an improved position of the transducer array 6. The user may then be instructed to move the ultrasound transducer array 6 to a better position shown in FIG. 4B. The transmit beam is then directed perpendicularly to the membrane to provide a resonant excitation resulting in the maximum intensity of the reflected echo signal 62 towards the direction of the transducer array 6.

An indicator 64 again for example provides a measure of the resonant signal strength so that the user can be directed to move the transducer array 6 to obtain the best location signal.

By receiving echo signals normally the acoustic sensor 52 has improved signal-to-noise-ratio for the analysis. By providing the transmit beam normally to the membrane surface, the resonance excitation is improved.

There may be a loss of signal strength when the relative position of the transducer array and the acoustic sensors varies, if the transducer array position is fixed for a relatively longer period. The signal processing may compare signal strengths derived from several adjacent transmit beams and select the beam that results in the highest signal strength from acoustic sensor. This can happen intermittently throughout the monitoring period and the selected beam can be updated and used as reference for position and signal strength.

The examples above are based on a single external transducer array. However, multiple transducer arrays may be used, each of which behaves similarly to cover larger areas.

The imaging capability of an ultrasound system is described above. However, for the purposes of location, there is no need to provide an ultrasound image to the end user. Thus, the invention in its most basic form may simply provide location information for example for the purposes of then performing a sensor measurement, and there may be no need for an actual ultrasound image to be produced. Of course, in many cases, the location function goes hand in hand with an imaging function so that the identified location is presented in combination with an image of the surrounding area.

Frequency analysis is performed in respect of the received signals. This may for example be performed by the controller 18. The frequency analysis is for example to identify the Doppler shift of the received signals in relation to the transmitted beams. This general method of identifying a resonant frequency of a resonator, such as an ultrasonic sensor, is for example described in US 2004/0211260.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A device for determining a location of an acoustic sensor within a subject, the device comprising:
   an ultrasound transducer array arranged to transmit a plurality of transmit beams in the subject and to receive corresponding reflected echo signals, including reflected echo signals from the acoustic sensor; and
   at least one controller for controlling the ultrasound transducer array to transmit the plurality of transmit beams according to an adaptive beam pattern, and for analyzing the reflected echo signals,
   wherein the at least one controller is adapted to implement a location process which comprises:
   performing frequency analyses of the received reflected echo signals responsive to the plurality of transmit beams to identify the reflected echo signals from the acoustic sensor;
   identifying a location area of the acoustic sensor using the identified reflected echo signal from the acoustic sensor responsive to a first non-focused transmit beam of the plurality of transmit beams; and
   deriving a progressively more accurate final location of the acoustic sensor within the location area; using at least one additional identified reflected echo signal from the acoustic sensor, responsive to at least one subsequent focused transmit beam of the plurality of transmit beams adjusted according to the adaptive beam pattern.

2. The device as claimed in claim 1, wherein the location process further comprises iteratively providing multiple transmit beams for successively smaller regions of interest with successively smaller depths of field and obtaining successively more accurate location areas of the acoustic sensor to derive the progressively more accurate final location.

3. The device as claimed in claim 1, wherein the location process comprises:
scanning a first plurality of focused transmit beams across a region of interest to provide focusing positions with a first spacing; and
scanning at least a second plurality of focused transmit beams across the region of interest to provide more closely spaced focusing positions.

4. The device as claimed in claim 1, wherein the at least one controller is further adapted to identify an orientation of the acoustic sensor.

5. The device as claimed in claim 4, wherein the at least one controller is adapted to identify the orientation of the acoustic sensor by determining a transmission angle of the first transmit beam and corresponding reflection angle for which the reflected echo signal from the acoustic sensor is strongest.

6. The device as claimed in claim 4, further comprising an output for directing a user to move the ultrasound transducer array to a location which gives a strongest reflected echo signal from the acoustic sensor.

7. The device as claimed in claim 1, wherein the ultrasound transducer array comprises a 2D array of transducer elements.

8. A location system comprising:
the acoustic sensor; and
the device as claimed in claim 1.

9. The system as claimed in claim 8, wherein the acoustic sensor comprises a membrane having a resonant frequency within a reception frequency range of the ultrasound transducer array, wherein the membrane generates the reflected echo signal at the resonant frequency.

10. A method of locating an acoustic sensor within a subject, the method comprising:
controlling transmission of ultrasound signals from an ultrasound transducer array to provide a plurality of transmit beams in the subject according to an adaptive beam pattern, each transmit beam comprising a transmission from each transducer of the ultrasound transducer array;
receiving reflected echo signals, including reflected echo signals from the acoustic sensor, responsive to the plurality of transmit beams;
performing frequency analyses of the received reflected echo signals to identify the reflected echo signals from the acoustic sensor;
determining a location area of the acoustic sensor using the identified reflected echo signal from the acoustic sensor responsive to a first non-focused transmit beam of the plurality of transmit beams;
and deriving a progressively more accurate final location of the acoustic sensor within the location area using at least one additional identified reflected echo signal reflected from the acoustic sensor responsive to at least one additional focused transmit beam of the plurality of transmit beams adjusted according to the adaptive beam pattern.

11. The method as claimed in claim 10, wherein the method further comprises: scanning a first plurality of focused transmit beams across a region of interest to provide focusing positions with a first spacing; and scanning at least a second plurality of focused transmit beams across the region of interest to provide more closely spaced focusing positions.

12. The method as claimed in claim 10, further comprising identifying an orientation of the acoustic sensor by determining a transmission angle and corresponding reflection angle for which the received echo signal from the acoustic sensor is strongest.

13. A non-transitory computer readable medium storing instructions for locating an acoustic sensor within a subject according to an adaptive beam pattern, using an ultrasound transducer array comprising a plurality of transducers, that when executed by at least one processor, the instructions cause the at least one processor to:
control transmission of ultrasound signals from the ultrasound transducer array to provide a plurality of transmit beams in the subject, each transmit beam comprising a transmission from each transducer of the plurality of transducers;
receive reflected echo signals, including reflected echo signals from the acoustic sensor, responsive to the plurality of transmit beams;
performing frequency analyses of the received reflected echo signals responsive to the plurality of transmit beams to identify the reflected echo signals from the acoustic sensor;
determine a location area of the acoustic sensor using the identified reflected echo signal from the acoustic sensor responsive to a first non-focused transmit beam of the plurality of transmit beams; and
deriving a progressively more accurate final location of the acoustic sensor within the location area using at least one additional identified reflected echo signal from the acoustic sensor, responsive to at least one additional focused transmit beam of the plurality of transmit beams adjusted according to the adaptive beam pattern.

14. The non-transitory computer readable medium as claimed in claim 13, wherein the instructions further cause the at least one processor to: scan a first plurality of focused transmit beams across a region of interest to provide focusing positions with a first spacing; and scan at least a second plurality of focused transmit beams across the region of interest to provide more closely spaced focusing positions.

15. The device as claimed in claim 1, wherein the adaptive beam pattern comprises starting as a non-focused broad beam pattern and narrowing to a focused beam pattern having a smaller beam width.

16. The method as claimed in claim 10, wherein the adaptive beam pattern comprises starting as a non-focused broad beam pattern and narrowing to a focused beam pattern having a smaller beam width.

17. The method as claimed in claim 12, further comprising directing a user to move the ultrasound transducer array to a location which gives a strongest location signal.

* * * * *